(12) United States Patent
Reilly et al.

(10) Patent No.: US 6,733,478 B2
(45) Date of Patent: May 11, 2004

(54) SYSTEM AND METHOD FOR PROVIDING INFORMATION FROM A SYRINGE TO AN INJECTOR

(75) Inventors: David M. Reilly, Glenshaw, PA (US); Joseph B. Havrilla, Pittsburgh, PA (US); Eugene A. Gelblum, Pittsburgh, PA (US); Daniel Kazousky, Templeton, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 10/287,167

(22) Filed: Nov. 4, 2002

(65) Prior Publication Data

US 2003/0060754 A1 Mar. 27, 2003

Related U.S. Application Data

(60) Continuation of application No. 09/611,939, filed on Jul. 7, 2000, now Pat. No. 6,475,192, which is a continuation of application No. 09/192,728, filed on Nov. 16, 1998, now Pat. No. 6,090,064, which is a division of application No. 08/901,602, filed on Jul. 28, 1997, now Pat. No. 5,997,502, which is a continuation of application No. 08/780,012, filed on Dec. 23, 1996, now Pat. No. 5,741,232, which is a continuation of application No. 08/359,087, filed on Jan. 19, 1995, now abandoned, which is a division of application No. 07/929,926, filed on Aug. 17, 1992, now Pat. No. 5,383,858.

(51) Int. Cl.$^7$ ................................................. A61M 5/00
(52) U.S. Cl. ...................... 604/189; 604/154; 604/118; 128/DIG. 1
(58) Field of Search ............................ 604/65, 67, 111, 604/118, 131, 189, 154, 151, 218, 152, 228, 135; 128/DIG. 1; 235/375, 435, 448, 454, 462, 453; 116/227

(56) References Cited

U.S. PATENT DOCUMENTS

| | | |
|---|---|---|
| 1,988,480 A | 1/1935 | Campkin |
| 2,702,547 A | 2/1955 | Glass |
| 3,051,173 A | 8/1962 | Johnson et al. |
| 3,604,417 A | 9/1971 | Stolzenberg |

(List continued on next page.)

FOREIGN PATENT DOCUMENTS

| | | |
|---|---|---|
| DE | 29 19 978 | 11/1980 |
| DE | 32 27 417 | 2/1983 |
| DE | 40 17 920 | 12/1991 |
| DE | 196 01 214 | 8/1996 |
| DE | 196 33 530 | 2/1998 |

(List continued on next page.)

OTHER PUBLICATIONS

Brochure for "Angiomat CT" of Liebel–Flarsheim, 2111 E. Galbraith Road, Cincinnati, OH 45215, Copyright 1988.
Brochure for "PercuPump 1A" of E–Z–EM, Inc., 717 Main Street, Westbury, NY 11590, Copyright 1990.

(List continued on next page.)

*Primary Examiner*—Manuel Mendez
*Assistant Examiner*—Cris L. Rodriguez
(74) *Attorney, Agent, or Firm*—Gregory L. Bradley

(57) ABSTRACT

A front-loading syringe which comprises a movable plunger for injecting liquid contrast media, is rotatably mountable on a front wall of an injector housing with an interference fit and in sealed relationship with respect thereto, with or without a pressure jacket, by a first-quick release mechanism. At the same time, the plunger is connected to an injector drive mechanism by a second readily releasable mechanism. During the mounting operation, a sensor reads injection information from an indicator device on the syringe and feeds it to an injector control. An audible-and-tactile indicating mechanism also is activated when the syringe is essentially in the desired mounted position. The syringe may include reinforcing ribs, which also function as volumetric gradations, and liquid media presence-or-absence indicating dots which appear circular against a liquid media background and oval-shaped against an air background. An injection end of the syringe comprises an injector portion of reduced diameter inside a screw-threaded attachment portion of larger diameter, and may include loop-shaped reinforcing handle portions.

12 Claims, 6 Drawing Sheets

U.S. PATENT DOCUMENTS

| | | |
|---|---|---|
| 3,623,474 A | 11/1971 | Heilman et al. |
| 3,645,262 A | 2/1972 | Harrigan |
| 3,701,345 A | 10/1972 | Heilman et al. |
| 3,720,211 A | 3/1973 | Kyrias |
| 3,738,539 A | 6/1973 | Beich |
| 3,752,145 A | 8/1973 | Runnells et al. |
| 3,796,218 A | 3/1974 | Burke et al. |
| 3,812,843 A | 5/1974 | Wootten et al. |
| 3,964,139 A | 6/1976 | Kleinmann et al. |
| 3,987,940 A | 10/1976 | Tischlinger |
| 4,006,736 A | 2/1977 | Kranys et al. |
| 4,030,498 A | 6/1977 | Tompkins |
| 4,080,967 A | 3/1978 | O'Leary |
| 4,155,490 A | 5/1979 | Glenn |
| 4,226,236 A | 10/1980 | Genese |
| 4,252,118 A | 2/1981 | Richard et al. |
| 4,278,086 A | 7/1981 | Hodgins et al. |
| 4,345,595 A | 8/1982 | Whitney et al. |
| 4,351,332 A | 9/1982 | Whitney et al. |
| 4,356,822 A | 11/1982 | Winstead-Hall |
| 4,424,720 A | 1/1984 | Bucchianeri |
| 4,452,251 A | 6/1984 | Heilman |
| 4,453,934 A | 6/1984 | Gahwiler et al. |
| 4,464,265 A | 8/1984 | Joyner |
| 4,465,472 A | 8/1984 | Urbaniak |
| 4,465,473 A | 8/1984 | Ruegg |
| 4,475,666 A | 10/1984 | Bilbrey et al. |
| 4,476,381 A | 10/1984 | Rubin |
| 4,493,646 A | 1/1985 | Lacour et al. |
| 4,529,401 A | 7/1985 | Leslie et al. |
| 4,568,335 A | 2/1986 | Updike et al. |
| 4,573,978 A | 3/1986 | Reilly |
| 4,585,439 A | 4/1986 | Michel |
| 4,604,847 A | 8/1986 | Moulding, Jr. et al. |
| 4,612,010 A | 9/1986 | Hamacher et al. |
| 4,617,016 A | 10/1986 | Blomberg |
| 4,636,198 A | 1/1987 | Stade |
| 4,648,872 A | 3/1987 | Kamen |
| 4,650,475 A | 3/1987 | Smith et al. |
| 4,652,260 A | 3/1987 | Fenton, Jr. et al. |
| 4,664,128 A | 5/1987 | Lee |
| 4,676,776 A | 6/1987 | Howson |
| 4,677,980 A | 7/1987 | Reilly et al. |
| 4,681,566 A | 7/1987 | Fenton, Jr. et al. |
| 4,685,903 A | 8/1987 | Cable et al. |
| 4,695,271 A | 9/1987 | Goethel |
| 4,705,509 A | 11/1987 | Stade |
| 4,722,734 A | 2/1988 | Kolln |
| 4,741,732 A | 5/1988 | Crankshaw et al. |
| 4,741,736 A | 5/1988 | Brown |
| 4,749,109 A | 6/1988 | Kamen |
| 4,755,172 A | 7/1988 | Baldwin |
| 4,767,406 A | 8/1988 | Wadham et al. |
| 4,773,900 A | 9/1988 | Cochran |
| 4,838,857 A | 6/1989 | Strowe et al. |
| 4,840,616 A | 6/1989 | Banks |
| 4,842,581 A | 6/1989 | Davis |
| RE32,974 E | 7/1989 | Porat et al. |
| 4,853,521 A | 8/1989 | Claeys et al. |
| 4,854,324 A | 8/1989 | Hirschman et al. |
| 4,869,720 A | 9/1989 | Chernack |
| 4,878,896 A | 11/1989 | Garrison et al. |
| 4,911,695 A | 3/1990 | Linder |
| 4,929,238 A | 5/1990 | Baum |
| 4,936,833 A | 6/1990 | Sams |
| 4,943,279 A | 7/1990 | Samiotes et al. |
| 4,966,601 A | 10/1990 | Draenert |
| 4,969,874 A | 11/1990 | Michel et al. |
| 4,973,309 A | 11/1990 | Sultan |
| 4,978,335 A | 12/1990 | Arthur, III |
| 4,988,337 A | 1/1991 | Ito |
| 5,007,904 A | 4/1991 | Densmore et al. |
| 5,033,650 A | 7/1991 | Colin et al. |
| 5,034,004 A | 7/1991 | Crankshaw |
| 5,047,014 A | 9/1991 | Mosebach et al. |
| 5,078,683 A | 1/1992 | Sancoff et al. |
| 5,084,017 A | 1/1992 | Maffetone |
| 5,085,638 A | 2/1992 | Farbstein et al. |
| 5,085,643 A | 2/1992 | Larkin et al. |
| 5,093,079 A | 3/1992 | Bakaitis et al. |
| 5,104,374 A | 4/1992 | Bishko et al. |
| 5,106,379 A | 4/1992 | Leap |
| 5,135,507 A | 8/1992 | Haber et al. |
| 5,147,311 A | 9/1992 | Pickhard |
| 5,153,827 A | 10/1992 | Coutre et al. |
| 5,226,897 A | 7/1993 | Nevens et al. |
| 5,236,416 A | 8/1993 | McDaniel et al. |
| 5,242,408 A | 9/1993 | Jhuboo et al. |
| 5,254,086 A | 10/1993 | Palmer et al. |
| 5,254,101 A | 10/1993 | Trombley, III |
| 5,256,157 A | 10/1993 | Samiotes et al. |
| 5,269,762 A | 12/1993 | Armbruster et al. |
| 5,275,582 A | 1/1994 | Wimmer |
| 5,279,569 A | 1/1994 | Neer et al. |
| 5,282,792 A | 2/1994 | Imbert |
| 5,300,031 A | 4/1994 | Neer et al. |
| 5,317,506 A | 5/1994 | Coutre et al. |
| 5,324,273 A | 6/1994 | Discko, Jr. |
| 5,338,309 A | 8/1994 | Imbert |
| 5,342,298 A | 8/1994 | Michaels et al. |
| 5,354,287 A | 10/1994 | Wacks |
| 5,356,375 A | 10/1994 | Higley |
| 5,356,393 A | 10/1994 | Haber et al. |
| 5,383,858 A | 1/1995 | Reilly et al. |
| 5,425,716 A | 6/1995 | Kawasaki et al. |
| 5,429,602 A | 7/1995 | Hauser |
| 5,429,611 A | 7/1995 | Rait |
| 5,431,627 A | 7/1995 | Pastrone et al. |
| 5,433,712 A | 7/1995 | Stiles et al. |
| 5,439,452 A | 8/1995 | McCarty |
| 5,445,622 A | 8/1995 | Brown |
| 5,451,211 A | 9/1995 | Neer et al. |
| 5,456,670 A | 10/1995 | Neer et al. |
| 5,520,653 A | 5/1996 | Reilly et al. |
| 5,531,698 A | 7/1996 | Olsen |
| 5,533,981 A | 7/1996 | Mandro et al. |
| 5,535,746 A | 7/1996 | Hoover et al. |
| 5,545,140 A | 8/1996 | Conero et al. |
| 5,573,515 A | 11/1996 | Wilson et al. |
| 5,658,261 A | 8/1997 | Neer et al. |
| 5,662,612 A | 9/1997 | Niehoff |
| 5,681,285 A | 10/1997 | Ford et al. |
| 5,681,286 A | 10/1997 | Niehoff |
| 5,683,367 A | 11/1997 | Jordan et al. |
| 5,738,659 A | 4/1998 | Neer et al. |
| 5,741,227 A | 4/1998 | Sealfon |
| 5,741,232 A | 4/1998 | Reilly et al. |
| 5,779,675 A | 7/1998 | Reilly et al. |
| 5,795,333 A | 8/1998 | Reilly et al. |
| 5,808,203 A | 9/1998 | Nolan, Jr. et al. |
| 5,827,219 A | 10/1998 | Uber, III et al. |
| 5,865,805 A | 2/1999 | Ziemba |
| 5,873,861 A | 2/1999 | Hitchins et al. |
| 5,882,343 A | 3/1999 | Wilson et al. |
| 5,899,885 A | 5/1999 | Reilly et al. |
| 5,913,844 A | 6/1999 | Ziemba et al. |
| 5,919,167 A | 7/1999 | Mulhauser et al. |
| 5,938,639 A | 8/1999 | Reilly et al. |
| 5,944,694 A | 8/1999 | Hitchins et al. |
| 5,947,929 A | 9/1999 | Trull |
| 5,947,935 A | 9/1999 | Rhinehart et al. |

| | | | |
|---|---|---|---|
| 5,954,697 A | 9/1999 | Srisathapat et al. | |
| 5,954,700 A | 9/1999 | Kovelman | |
| 5,997,502 A | 12/1999 | Reilly et al. | |
| 6,048,334 A | 4/2000 | Hirschman et al. | |
| 6,059,756 A | 5/2000 | Yeh | |
| 6,080,136 A | 6/2000 | Trull et al. | |
| 6,083,197 A | 7/2000 | Umbaugh | |
| 6,090,064 A | 7/2000 | Reilly et al. | |
| 6,099,502 A | 8/2000 | Duchon et al. | |
| 6,221,045 B1 | 4/2001 | Duchon et al. | |
| RE37,487 E | 12/2001 | Reilly et al. | |

FOREIGN PATENT DOCUMENTS

| | | |
|---|---|---|
| EP | 0 160 303 | 11/1985 |
| EP | 0 164 904 | 12/1985 |
| EP | 0 320 168 | 6/1989 |
| EP | 0 323 321 | 7/1989 |
| EP | 0 346 950 | 12/1989 |
| EP | 0 364 010 | 4/1990 |
| EP | 0 384 657 | 8/1990 |
| EP | 0 482 677 | 4/1992 |
| EP | 0 523 343 | 1/1993 |
| EP | 0 567 944 | 11/1993 |
| EP | 0 584 531 | 3/1994 |
| EP | 0 736 306 | 10/1996 |
| EP | 0 749 757 | 12/1996 |
| EP | 0 900 573 | 3/1999 |
| EP | 0 919 251 | 6/1999 |
| GB | 847914 | 1/1961 |
| GB | 1 380 873 | 1/1975 |
| GB | 2 108 852 | 5/1983 |
| JP | 61-500415 | 3/1986 |
| JP | 63-68177 | 3/1988 |
| WO | WO 80/02376 | 11/1980 |
| WO | WO 85/00292 | 1/1985 |
| WO | WO 85/02256 | 5/1985 |
| WO | WO 89/06145 | 7/1989 |
| WO | WO 89/09071 | 10/1989 |
| WO | WO 89/11310 | 11/1989 |
| WO | WO 90/01962 | 3/1990 |
| WO | WO 91/04759 | 4/1991 |
| WO | WO 92/21391 | 12/1992 |
| WO | WO 94/25089 | 11/1994 |
| WO | WO 96/32975 | 10/1996 |
| WO | WO 97/36635 | 10/1997 |
| WO | WO 99/65548 | 12/1999 |
| WO | WO 01/37905 | 5/2001 |
| WO | WO 02/04049 | 1/2002 |

OTHER PUBLICATIONS

Medrad, Mark V/Mark V Plus Injector Operation Manual, KMP 805P, Rev B (1990); pp. 1–18 to 1–28, 3–7 to 3–13, 14–1 to 14–4.

Brochure for the "The First and Only True Injection System," Medrad Mark V System, Control No. 85106–00–BA–02, 11/88.

Injektron 82 MRT User Instruction, Version MR2,CEO535, Med–Tron GmbH, (Mar. 10, 1999).

Brochure for "Cordis Lymphography Injector," Cordis Corporation, Miami, FL 33137 (1972).

Medrad Envision CT Injector Operation Manual, EOM 700E, 92401–T–123, Rev. E, Copyright 1995.

Liebel–Flarsheim Company, Angiomat 6000 Digital Injection System Operator's Manual, 600950 Rev 1; pp. 3–6 to 3–8, 4–52 to 4–56 (1990).

Brochure for "Angiomet 6000" of Liebel–Flarsheim, 2111 E. Galbraith Road, Cincinnati, OH 45215, copyright 1987.

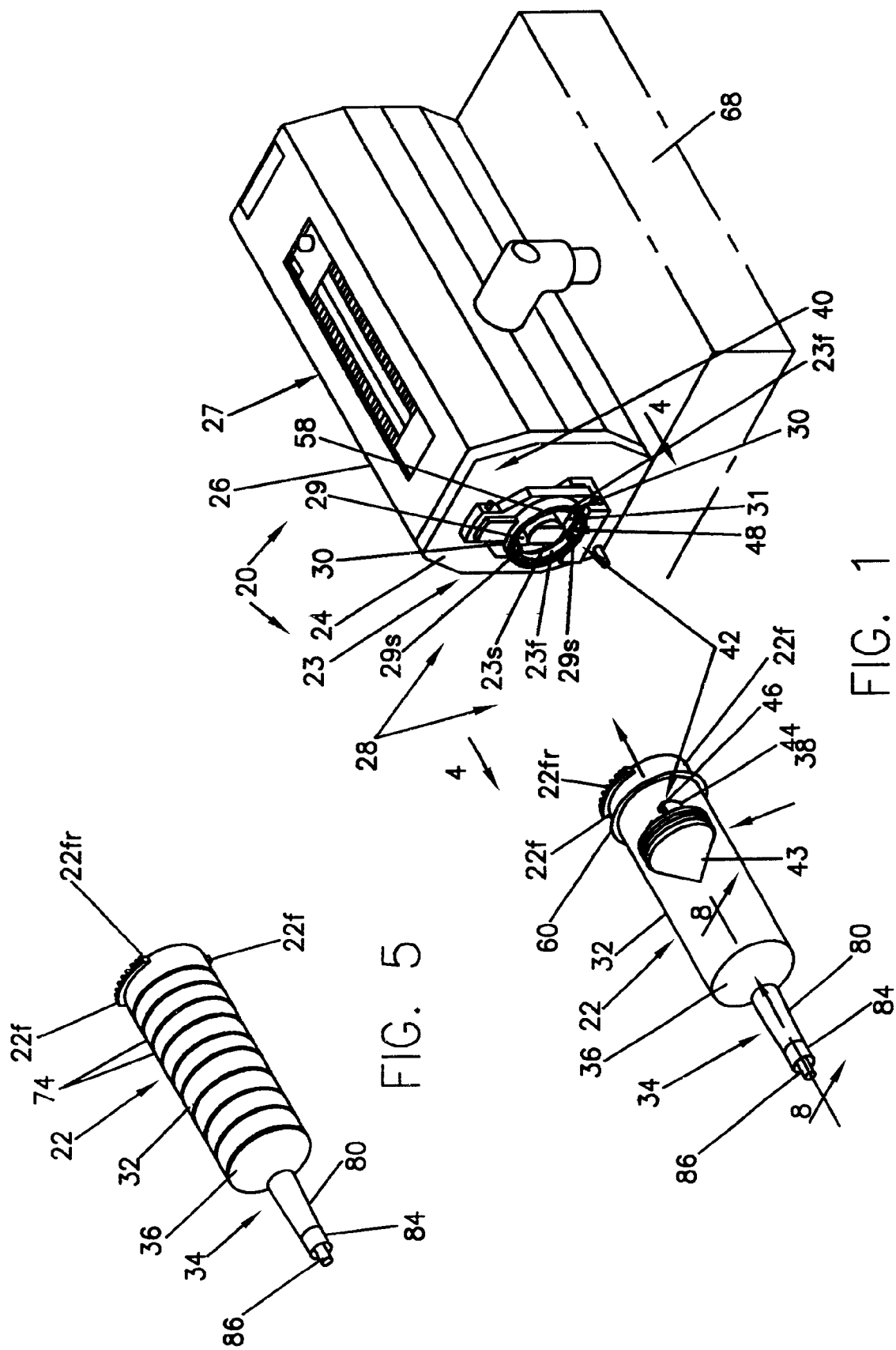

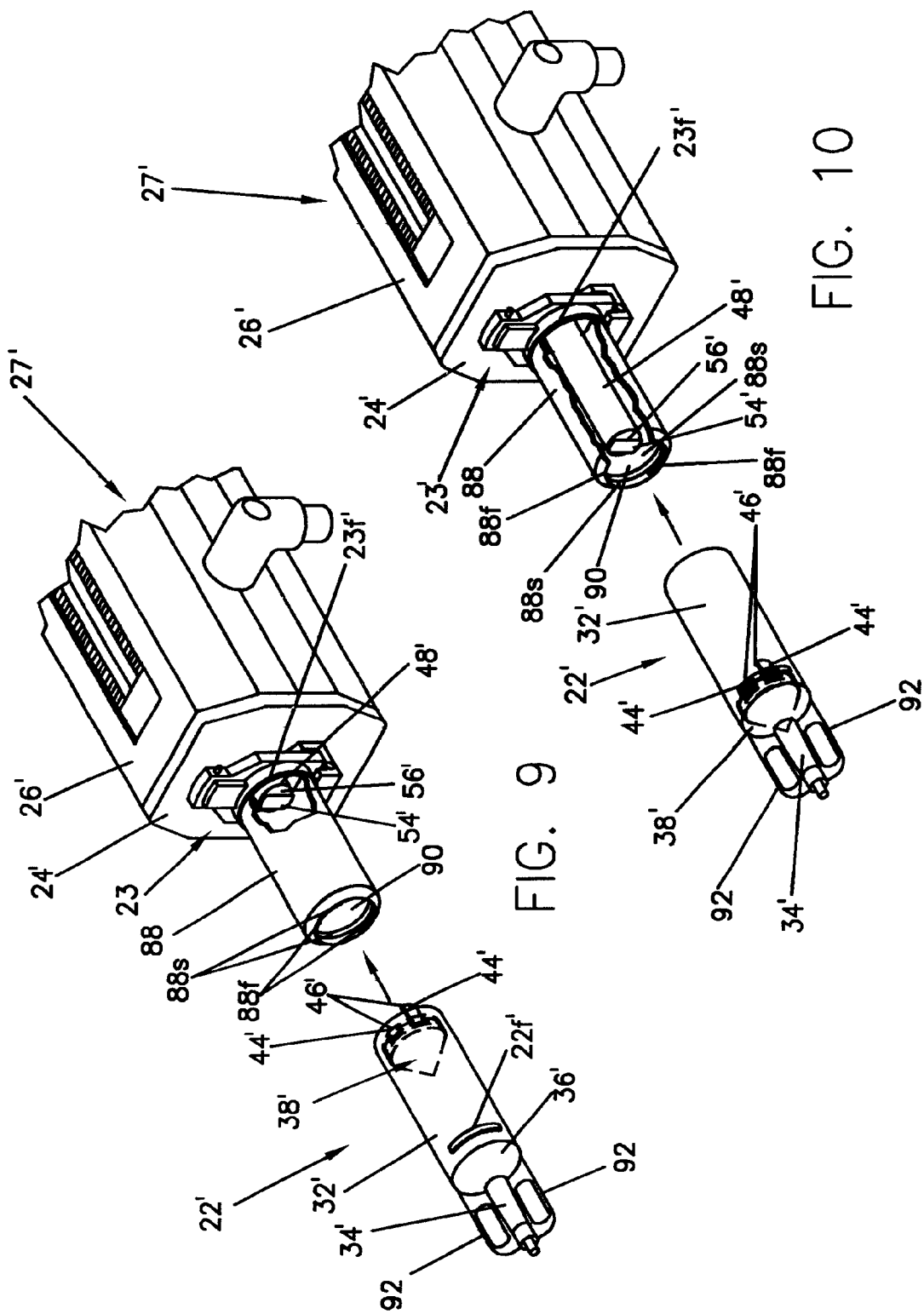

SYSTEM AND METHOD FOR PROVIDING INFORMATION FROM A SYRINGE TO AN INJECTOR

CROSS-REFERENCE TO RELATED APPLICATIONS

This application is a continuation of application Ser. No. 09/611,939, filed on Jul. 7, 2000, now U.S. Pat. No. 6,475,192, which is a continuation of application Ser. No. 09/192,728, filed on Nov. 16, 1998, now U.S. Pat. No. 6,090,064, which is a division of application Ser. No. 08/901,602, filed on Jul. 28, 1997, now U.S. Pat. No. 5,997,502, which is a continuation of application Ser. No. 08/780,012, filed on Dec. 23, 1996, now U.S. Pat. No. 5,741,232, which is a continuation of application Ser. No. 08/359,087, filed on Jan. 19, 1995, abandoned, which is a division of application Ser. No. 07/929,926, filed on Aug. 17, 1992, now U.S. Pat. No. 5,383,858.

BACKGROUND OF THE INVENTION

This invention relates to a front-loading medical injector and a syringe for use therewith, and more particularly to a front-loading medical injector apparatus wherein a syringe of special construction is mountable upon and removable from a front wall of an injector housing by a first readily releasable mechanism, while a plunger in the syringe is simultaneously connected to or dissembled from an injector drive member by a second readily releasable mechanism.

U.S. Pat. No. 4,006,736, issued to R. J. Kranys et al. on Feb. 8, 1977, and entitled, "Angiographic Injector", which is assigned to the same Assignee as the subject application, discloses an angiographic injector apparatus for injecting contrast media into the vascular system of an animal, in which angiographic syringes are rear-loaded into a pressure jacket of the injector. More specifically, the apparatus comprises a rotatable turret which carries a pair of the pressure jackets and which is rotatable so that when one of the pressure jackets, into which an angiographic syringe has been rear-loaded, is in an injection position, the other pressure jacket is in a position in which an associated angiographic syringe can be rear-loaded. Subsequently, when injection of contrast media from the first syringe is completed, the turret is rotated to move the first syringe to an unloading-loading position, with the second pressure jacket and the angiographic syringe then being moved into the injection position. In this apparatus, when each of the pressure jackets and its associated syringe has been located in the injection position, a drive member of the injector is moved forward to become drivingly engaged with a plunger in the syringe; however, the manner of engagement between the drive member and plunger is such that the drive member cannot be retracted without also retracting the plunger, which can cause body fluids of the animal to be retracted into the syringe unless the syringe is first disconnected from the animal.

An improved apparatus over the apparatus as disclosed in the Kranys et al. patent, is disclosed in U.S. Pat. No. 4,677,980, issued to D. M. Reilly et al. on Jul. 7, 1987, and entitled "Angiographic Injector and Angiographic Syringe for Use Therewith", which also is assigned to the same Assignee as the subject application, In this apparatus, a drive member of the angiographic injector can be drivingly connected to, or disconnected from, a plunger of an angiographic syringe at any point along the path of travel of the plunger by a readily releasable mechanism. Thus, the apparatus of the Reilly et al. patent represented certain improvements over the Kranys et al. patent. However, the apparatus of the Reilly et al. patent, like that of the Kranys et al. patent, is of a rear-loading type comprising a pair of pressure jackets mounted upon a rotatable turret for moving the pressure jackets and syringes therein between injection and loading positions.

Accordingly, a need exists for a front-loading medical injector and a syringe of special construction so that the syringe can be readily and securely front-loaded directly and accurately in a desired position on the injector, thereby facilitating the loading-unloading operation, and a primary purpose of this invention is to provide such an arrangement with its various attendant advantages. Further, in certain instances, it is desirable that the syringe not be enclosed in a pressure jacket, in order that an operator be able to view the status of the syringe visually during an injection operation. By allowing the operator to see the syringe, the operator can, e.g., determine whether the syringe is empty or full, determine if it is being filled too fast and/or introducing too many air bubbles, when the syringe is filled, and the amount of contrast that has been delivered or remains in the syringe during a procedure. Another purpose of this invention is, in one embodiment, to provide an injector apparatus of such construction.

SUMMARY OF THE INVENTION

In general, in accordance with the invention, a readily releasable mechanism is provided for supporting a syringe on a front wall or an injector housing for an injection operation. For this purpose, the readily releasable mechanism includes at least one retaining portion on the mounting mechanism releasably engageable with a mating retaining portion on the syringe. Further, an actuating mechanism of the injector includes a drive member, which is connectable to a plunger in the syringe for controlling the movement of the plunger in the syringe.

More specifically, the readily releasable mechanism is an interlocking mechanism which is activated and released upon rotation of a rearward portion of the syringe relative to the front wall of the injector housing. At the same time, a second readily releasable interlocking mechanism for connecting the injector drive member to the syringe plunger, and which also is activated and released upon rotation of the syringe relative to the front wall of the housing, interconnects the drive member and the plunger. The first readily releasable mechanism may comprise a mounting mechanism on the front wall of the housing having at least a pair of slots for receiving retaining flanges on the rearward end of the syringe there through, with the syringe then being rotated to engage the flanges behind associated retaining flanges of the mounting mechanism. The second readily releasable mechanism comprises respective radially projecting parts on the drive member and the plunger, which become drivingly engaged in a similar manner upon rotation of the syringe and the plunger.

The first readily releasable mechanism may be further defined by the mounting mechanism on the injector housing front wall having an annular sealing member against which a resilient annular sealing member on the syringe becomes seated as the syringe is positioned on the mounting mechanism, with the resilient annular sealing member and the retaining flanges on the syringe receiving the retaining flanges on the mounting mechanism there between with an interference fit. An audible-and-tactile indicator mechanism, alignment arrows, and/or alignment dots also may be provided to detect when the syringe has been essentially rotated into its desired mounted position against suitable stops, with this mechanism then further functioning to discourage reverse rotation of the syringe on the injector housing. An indicator mechanism for providing liquid media injection information to an injector controller, and a sensor for reading the indicating mechanism, also may be provided on the syringe and the injector housing, respectively. The syringe also may include a mechanism which provides a visual indication of whether the syringe still includes injection liquid, may have an injector nozzle of reduced diameter surrounded by a screw-threaded cylindrical attachment portion at its injection end (the reduced diameter nozzle serving to minimize the amount of contrast that remains in the syringe after the plunger has been fully extended), may be provided with reinforcing ribs which are longitudinally spaced so as to also function as volumetric gradations, and/or may be formed of relatively strong clear plastic.

In another embodiment of the invention, which utilizes a pressure jacket, the pressure jacket is in the form of an elongated tube having one end mounted on the front wall of the injector housing, and having an opposite open outer end. In a syringe mounting operation, a syringe is inserted into the open end of the tubular jacket until an inner end of the syringe engages against a seat mechanism on the injector housing front wall. During this insertion operation, retaining flanges adjacent the forward end of the syringe pass through slots in the open end of the tubular pressure jacket, whereupon the syringe is rotated to engage the flanges behind corresponding mating retaining flanges at the open end of the jacket. As the syringe is rotated, a plunger in the syringe also rotates into driving engagement with a drive member of the injector. An outer injection end of the syringe also may be provided with reinforcing-handle members.

BRIEF DESCRIPTION OF THE DRAWINGS

FIG. 1 is a partial, isometric view of an injector apparatus in accordance with the invention, showing an injector housing and a syringe in disassembled relationship;

FIG. 5 is an isometric view of a modified form of the syringe shown in FIG. 1;

FIG. 9 is an isometric view similar to FIG. 1, illustrating an embodiment of the invention utilizing a pressure jacket, with an injector drive member and a syringe plunger in a retracted loading position;

FIG. 10 is an isometric view similar to FIG. 9, illustrating the apparatus of the pressure jacket embodiment with the injector drive member and the syringe plunger in an advanced loading position.

DESCRIPTION OF THE DISCLOSED EMBODIMENTS

Figure 6:
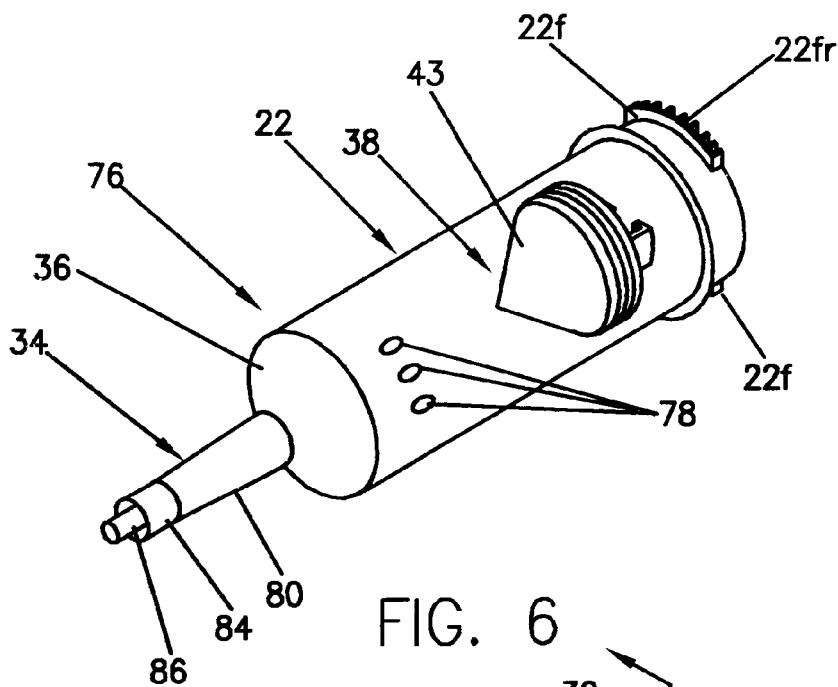
FIG. 6 is an enlarged isometric view of the syringe shown in FIG. 1, illustrating another feature of the invention.

FIG. 1 discloses an injector apparatus 20 of the general type disclosed in the U.S. Pat. No. 4,006,736 to R. J. Kranys et al. and U.S. Pat. No. 4,677,980 to D. M. Reilly et al., for injecting a liquid contrast media into a vascular system of an animal, but of front-loading construction, rather than rear-loading construction, as disclosed in those patents. Thus, the apparatus of FIG. 1 utilizes a syringe 22 capable of being front-loaded into a mounting assembly 23 on a front wall 24 of a housing 26 of an injector 27 by a first readily releasable mechanism 28, and also capable of functioning in an injection operation without the use of a pressure jacket, whereas each apparatus of those patents is of a type in which angiographic syringes are rear-loaded into respective pressure jackets supported on a rotatable turret for moving the jackets between injection and loading positions. However, to the extent not inconsistent with this disclosure, the disclosures of those two patents, which both are assigned to Medrad Inc, of Pittsburgh, Pa., the Assignee of the subject application, are hereby incorporated by reference.

Figure 2:
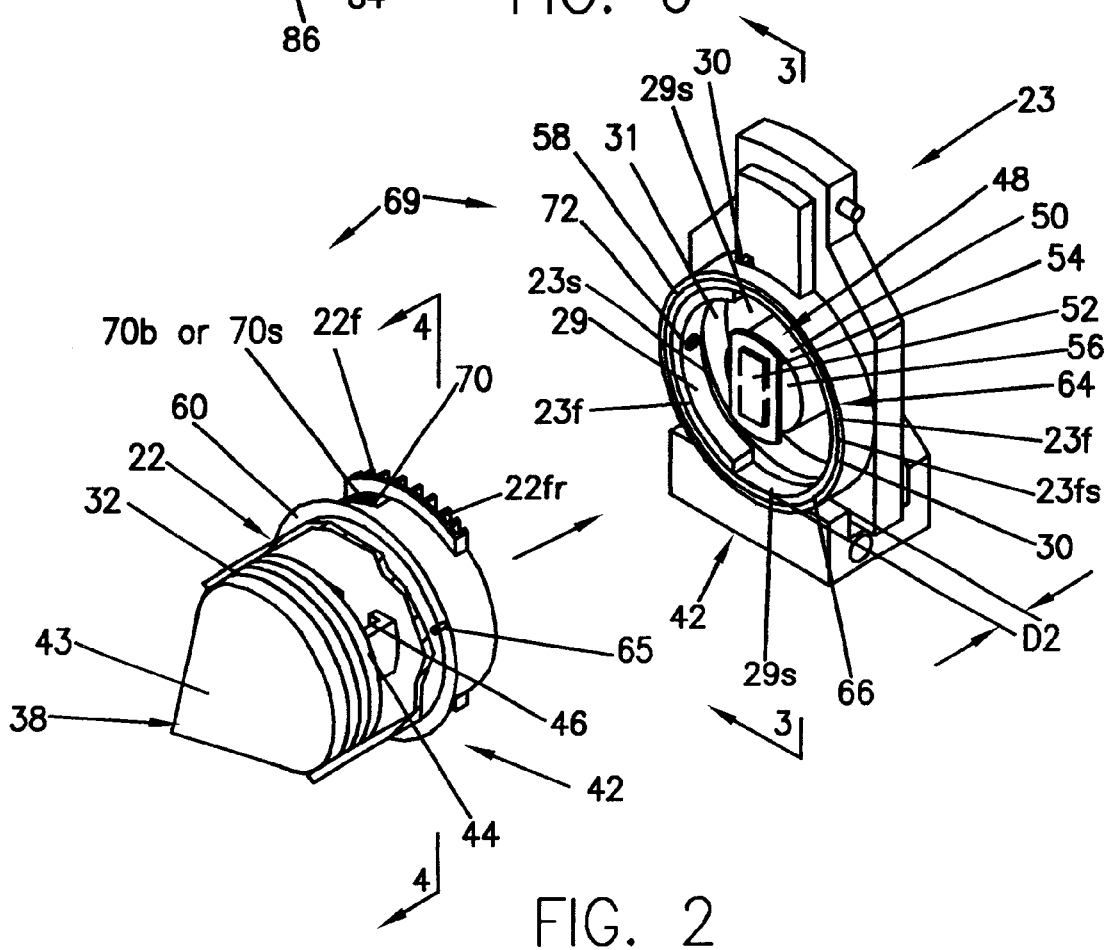
FIG. 2 is an enlarged isometric view of portions of the apparatus shown in FIG. 1, more specifically illustrating certain features of the invention.
Figure 3:
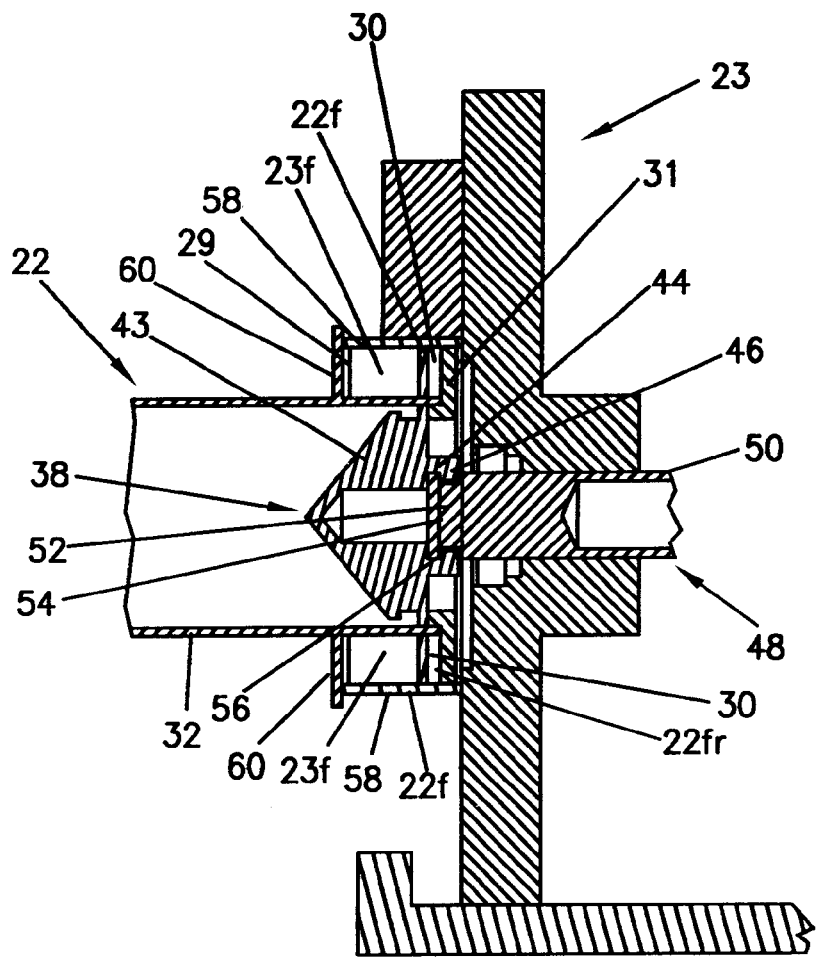
FIG. 3 is a partial, cross-sectional view, taken essentially along the line 3—3 in FIG. 1, illustrating the injector housing and the syringe in assembled relationship.

With reference to FIGS. 1–3 and the first readily releasable mechanism 28, the mounting assembly 23 on the front wall 24 of the injector housing 26 is provided with an essentially cylindrical opening 29 for receiving a rearward end of the syringe 22. The opening 29 includes a pair of upper and lower slots 29s (best shown in FIG. 2) through which respective upper and lower retaining flanges 22f of the syringe 22, having reinforcing ribs 22fr, may pass as the rearward end of the syringe is inserted in the opening. The mounting assembly 23 further includes opposed retaining flanges 23f on opposite sides thereof so that, after the rearward end of the syringe 22 has been inserted into the opening 29, and the syringe is rotated clockwise, as viewed in FIG. 1, the retaining flanges 22f on the syringe become engaged behind the retaining flanges 23f to secure the syringe to the housing front wall 24. During this mounting of the syringe 22 on the housing front wall 24, the rotation of the syringe preferably is limited by suitable rearwardly projecting stops 30 at adjacent ends of the housing front wall retaining flanges 23f. The mounting assembly 23 also includes an inner annular ring 31 in spaced relationship to the retaining flanges 23f, to provide support for the rearward end of the syringe 22 and also define semi-annular guide slots 23s (best shown in FIG. 2) for receiving the syringe flanges 22f.

Figure 4:
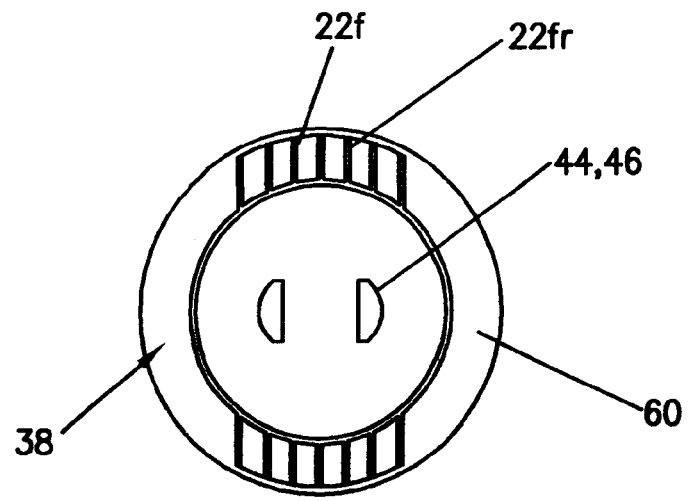
FIG. 4 is an end view, as seen essentially along the line 4—4 in FIG. 1, illustrating features of the syringe.

As is disclosed in the aforementioned D. M. Reilly et al U.S. Pat. No. 4,677,980, and referring again to FIG. 1, the syringe 22 comprises an elongated main tubular body or barrel 32 and a coaxial discharge injection section 34, interconnected by an intermediate conical portion 36. A plunger 38 is slidably positioned within the tubular body 32 and is connectable to an actuating mechanism 40 in the injector housing 26 by a second readily releasable mechanism 42. The second readily releasable mechanism 42 is formed in part by the plunger 38 comprising a base member 43 having hook or lug members 4 (FIGS. 1, 3 and 4) extending rearwardly therefrom, with portions 46 of these members extending radially inward in opposed relationship. The plunger 38 serves to control the ejection of fluid contained within the syringe 22 in a desired quantity and at a desired rate, and the hook members 44 are designed to facilitate axial movement of the plunger in either direction when connected to the actuating mechanism 40 by the second readily releasable mechanism 42.

Further in this connection, as is best shown in FIGS. 2 and 3, the actuating mechanism 40, which reciprocates the plunger 38 in the syringe tubular body 32, comprises a reciprocable drive member 48 which includes a base portion 50, a stem 52 (FIG. 3) and an integral rectangular head 54 extending radially outward from the stem, all of which form additional parts of the second readily releasable mechanism 42. The drive member 48, however, while reciprocable, is not rotatable, as disclosed in the above-mentioned Reilly et al patent. Rather, as the syringe 22 is inserted into the opening 29 in the mounting assembly 23, the hook members 44 (FIG. 3) on the plunger 38 initially move past the rectangular head 54 on the drive member 48 on opposite sides thereof into alignment with the stem 52 and slots 56 defined by the rectangular head and the base portion 50. Then, when the syringe 22 is rotated clockwise to engage the syringe retaining flanges 22f behind the retaining flanges 23f of the mounting assembly 23, the radially extending portions 46 of the hook members simultaneously move into the slots 56 to effect a driving engagement between the plunger 38 and the drive member 48 in either a forward or reverse direction, as is best shown in FIG. 3.

With further reference to FIGS. 1–3, the mounting assembly 23 further includes a forwardly projecting annular ring or collar 58 which functions to remove extra slack in the mounting slots and assure perpendicular engagement between the plunger 38 and the drive member 48, as well as for sealing. The retaining flanges 23f are mounted within the annular ring 58. As is illustrated in FIG. 2, the tubular body 32 of the syringe 22 also includes a resilient annular sealing ring 60 surrounding the tubular body and disposed forward of the syringe retaining flanges 22f a preselected distance D1 essentially equal to a thickness D2 of the mounting assembly retaining flanges 23f. Thus, when the syringe 22 is inserted into the opening 29 in the mounting assembly 23 until the syringe sealing ring 60 engages the annular ring 58, and is then rotated to engage the syringe retaining flanges 22f behind the retaining flanges 23f, the latter flanges are received between the syringe retaining flanges and the resilient syringe sealing ring with an interference fit. For this purpose, the retaining flanges 23f may be provided with a slight lead-in taper (not shown) to facilitate initial movement thereof between the syringe retaining flanges 22f and the resilient sealing ring 60.

Figure 7:
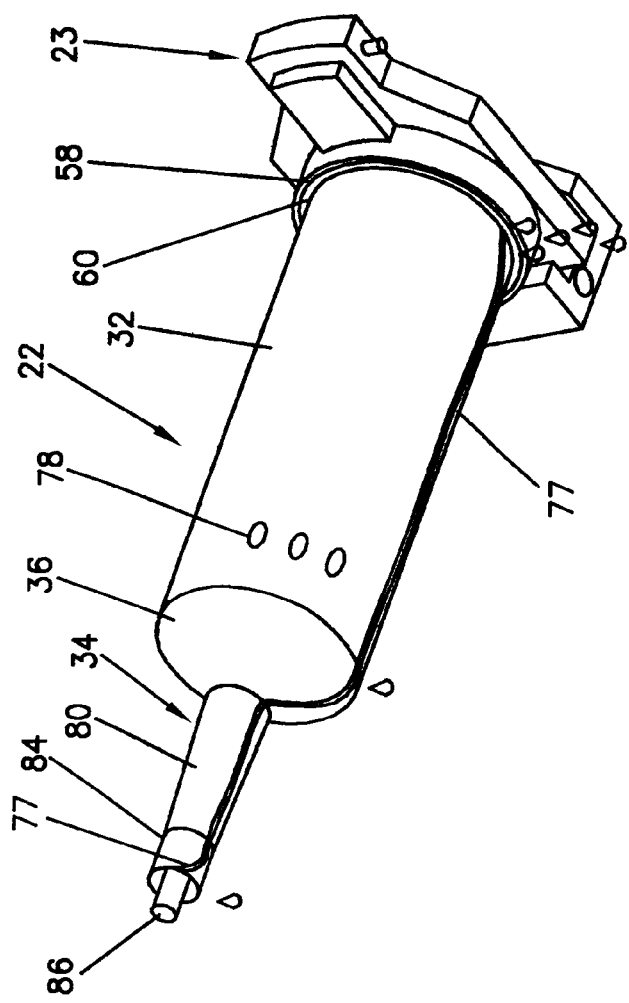
FIG. 7 is an isometric view of portions of the apparatus shown in FIG. 1 in a different orientation, illustrating a further feature of the invention.

The foregoing mounting arrangement possesses a number of advantages, including minimizing wobble and rotation of the syringe 22 during an injection operation, preventing unwanted rotational disengagement of the syringe from the injector housing 26, by creating a controlled sliding friction interference fit, preventing contrast media spilled from the injecting end of the syringe, from flowing into the injector housing 26, as illustrated in FIG. 7, and eliminating the need for constructing the respective parts to excessively tight tolerances. This tight-fitting mounting of the syringe 22 on the housing front wall 24 is further facilitated by providing the syringe retaining flanges 22f with the reinforcing ribs 22fr (FIGS. 1, 2 and 4) to enhance their structural rigidity. To enhance the sealing capability of the annular rings 58 and 60, a suitable O-ring (not shown) also may be provided there between.

Referring again to FIG. 2, in the disclosed embodiment of the invention, the resilient annular sealing ring 60 on the syringe 22 and at least one of the retaining flanges 23f of the mounting assembly 23 include respective parts which form an audible-and-tactile indicating mechanism 64 for detecting and indicating when the syringe and its plunger 38 have essentially been rotated into a desired mounted position against the stops 30. More specifically, the retaining flange 23f includes an arcuate slot 23fs formed in a front surface thereof for receiving a projection 65 on the syringe sealing flange 60 as the syringe is rotated relative to the injector housing front wall 24. The slot 22fs further includes a protuberance 66 spaced slightly from one end of the slot so that this protuberance is engaged by the projection 65 on the syringe sealing ring 60 during rotation of the syringe toward its mounted position, with this engagement providing an audible and tactile feedback indicating that the syringe is essentially in the mounted position. Then, as the syringe 22 continues to be rotated into its mounted position, the projection 65 on the syringe annular sealing ring 60 rides over the protuberance 66 in the slot 22fs and into a small space between the protuberance and the end of the slot, just before the retaining flanges 22f on the syringe engage their respective stops 30. The protuberance 66 in the slot 22fs then cooperates with the projection 65 to prevent undesired reverse rotation of the syringe 22 out of its mounted position. In the alternative, this arrangement may be reversed, with a slot-protuberance arrangement being provided on the syringe annular sealing ring 60, and a projection being provided on the one retaining flange 23f of the injector housing front wall mounting assembly 23. Moreover, although this embodiment describes the use of a projection and slot, one should recognize that other means may also accomplish the desired tactile/audible effect. Thus, for example, one may instead use a "dimple" located on the flange 60 which may snap into a receiving hole on the retaining flange 23f.

Figure 11A:
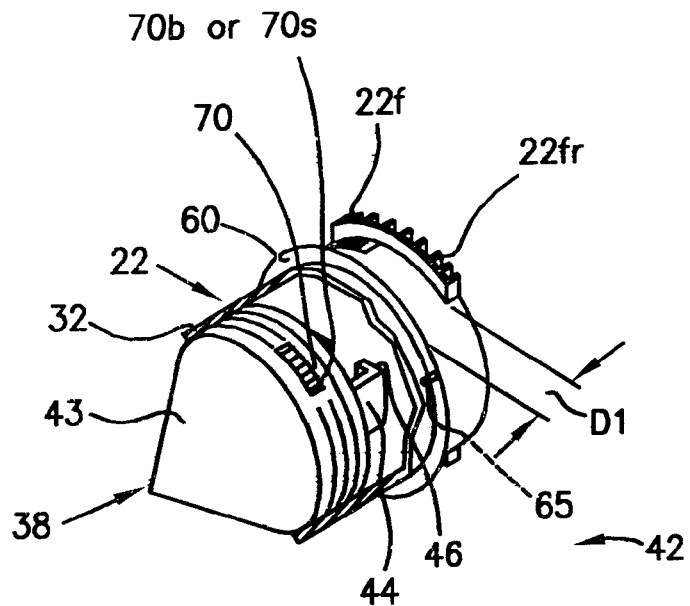
FIGS. 11a and 11b are enlarged isometric views, similar to FIG. 2, illustrating certain features of the invention.
Figure 11B:
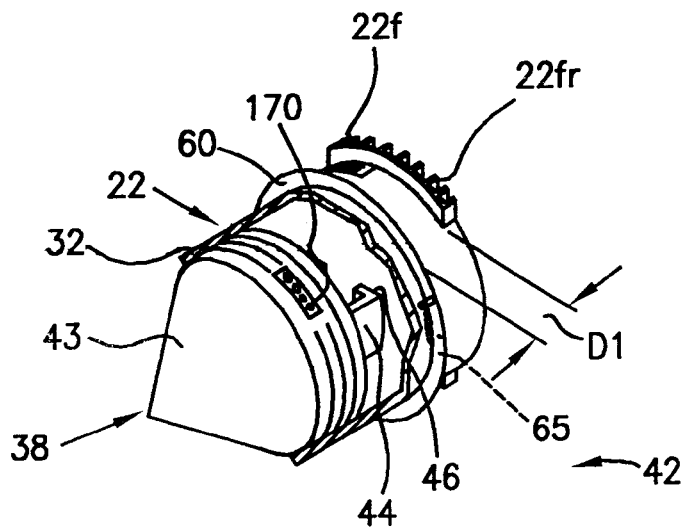

With further reference to FIGS. 2, 11a and 11b, a system 67 for transmitting syringe information from the syringe 22 to an injector controller 68, illustrated in phantom lines in FIG. 1, while attaching the syringe to the injector housing front wall mounting assembly 23, also is provided. In this instance, the system 67 comprises an encoding device 70, such as a bar code having spaced bars 70b and located on the syringe 22 or the syringe plunger 38, and a sensor 72 located on the injector 27, as for example, in a second one of the connector assembly retaining flanges 23f. Then, as the syringe 22 is rotated into its mounted position, the sensor 72 reads the encoding device 70 and forwards associated signals to the injector controller 68, which then interprets the signals and modifies the function of the injector apparatus 20 accordingly. Examples of the information which could be encoded on the encoding device 70 include dimensions of the syringe 22, content of the syringe in the case of a pre-filled syringe, manufacturing information such as lot numbers, dates and tool cavity number, recommended contrast media flow rates and pressures, and loading/injection sequences. As an alternative to the encoding device 70 being a bar code with spaced bars 70b, the encoding device also could include raised surfaces 70s corresponding to the spaced bars, which then would be read by a suitable injector sensor 72 in a similar manner, as the syringe 22 is mounted on the injector housing front wall 24. In addition to the encoding device 70, one may also use mechanically readable devices, e.g. a slot, hole, or projection on the syringe 22 or plunger 38 to register against a switch on the mounting assembly 23, or alternatively on optically readable device 170, e.g. characters, dots and other geometric shapes, that will send information concerning the type of syringe used to the intelligent circuits of the injector.

Referring to FIG. 5, since the syringe 22 is being used in this embodiment without a pressure jacket, for strength and visibility of the syringe contents, the syringe wall may be formed of a clear PET polyester material. In the alternative, the wall of the syringe 22 may be formed of polypropylene reinforced by providing a series of annular ribs 74 on the tubular body 32 of the syringe in longitudinally spaced relationship. Further, by suitably spacing the ribs 74 along the length of the tubular body 32, such as in equal increments, the ribs also can perform the dual function of serving as volumetric gradations for the purpose of indicating the amount of contrast media in the syringe 22.

With reference to FIG. 6, the tubular body 32 of the syringe 22 also may be provided with an indicating mechanism 76 for readily detecting the presence or absence of a liquid contrast media in the syringe. In this instance, the detecting mechanism 76 includes a plurality of integrally molded, textured dots 78 on the syringe 22, which provide a visual indication of whether the syringe contains liquid or air. More specifically, as illustrated in FIGS. 6 and 7, when viewed against an air background (FIG. 7), the dots 78 appear oval-shaped, but when viewed against a liquid contrast media background (FIG. 6), which has a different index of refraction than air, the dots 78 appear circular.

Figure 8:
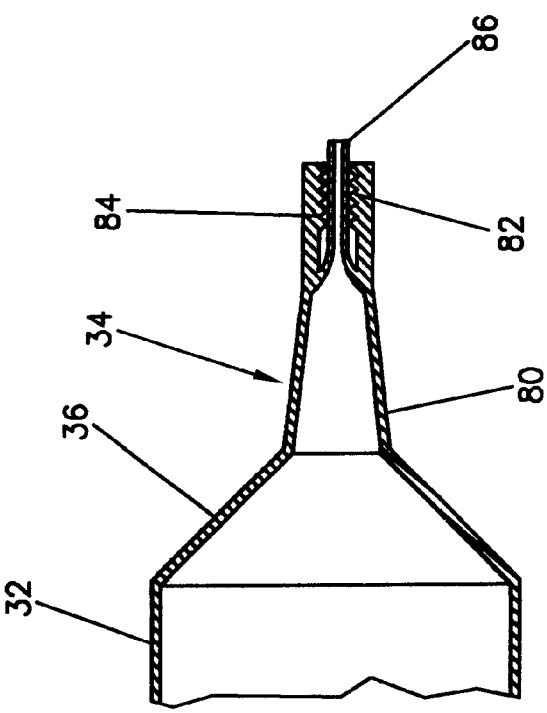
FIG. 8 is a cross-sectional view taken essentially along the line 8—8 in FIG. 1, illustrating another feature of the invention.

FIG. 8 illustrates the internal construction of the syringe discharge injection section 34. Specifically, while a rearward portion 80 of the injection section 34 is of tapered conical construction, a forward connector portion 82 is of generally cylindrical construction and formed with internal screw threads 84 for attaching a catheter (not shown) to the injection section. Further, an injection nozzle 86 of reduced diameter is disposed within the screw-threaded cylindrical connector portion 82 and is integrally molded with the tapered rearward portion 80 of the injection section adjacent the point at which the tapered and cylindrical portions merge together.

FIGS. 9 and 10 discloses an alternate embodiment of the invention in which a front-loading syringe 22' is mounted on a front wall 24' of a housing 26' of an injector 27' in conjunction with a pressure jacket 88, preferably formed of a strong clear plastic, such as polycarbonate. The pressure jacket 88 is in the form of an elongated tubular member which is suitably mounted at its rearward end in a mounting assembly 23' on the housing front wall 24', by fitting the flange of pressure jacket 88 into the collar on the mounting assembly 23'. The pressure jacket 88 also has a forward open end 90 for receiving the syringe 22'.

Thus, in this embodiment, a pair of opposed inwardly projecting retaining flanges 88f, separated by opposed slots 88s, are provided adjacent the forward open end of the pressure jacket 88, rather than in the mounting assembly 23' on the injector housing front wall 24' as in the embodiment of FIGS. 1–8. Similarly, a tubular body 32' of the syringe 22' also includes a pair of outwardly projecting retaining flanges 22f' (only one shown) on opposite sides thereof, but in this instance located adjacent the forward end of the tubular body, rather than adjacent its rearward end, as in the embodiment of FIGS. 1–8. In addition, at the forward end of the syringe 22', on opposite sides of a discharge injection section 34', a pair of reinforcing, loop-shaped handle portions 92, for facilitating handling of the syringe, including rotation thereof, are integrally molded with the injection section and a tapered conical intermediate portion 36'. In other respects, while not specifically disclosed and described, it is to be understood that various other features of the embodiment of the invention disclosed in FIGS. 1–8, may be incorporated into the embodiment of FIGS. 9 and 10, as desired.

In use, the syringe 22' of FIGS. 9 and 10 may be mounted in the pressure jacket 88 with a drive member 48' of the injector 27' either in a retracted position, as shown in FIG. 9, or in an advanced position, as shown in FIG. 10. For example, with the drive member 48' in the retracted position, as shown in FIG. 9, a plunger 38' is disposed at the rearward end of the syringe 22'. The syringe 22' then is inserted into the open end 90 in the forward end of the pressure jacket 88 until the rearward face of the retaining flanges 22f' have engaged against suitable seat members in the pressure jacket 88, with hook members 44' of the syringe plunger 38' having moved beyond a rectangular head 54' of the drive member 48' and into alignment with associated slots 56' in the drive member. At the same time, the retaining flanges 22f' on the syringe 22' have moved through the slots 88s at the forward end of the pressure jacket 88 into positions rearward of the retaining flanges 88f adjacent the opening 90 in the pressure jacket. The syringe 22' then is rotated clockwise in FIG. 9, using the handles 92, to move radially projecting portions 46' of the hook members 44' on the syringe plunger 38' into the slots 56' of the drive member 48', and to simultaneously move the retaining flanges 22f' on the syringe into engagement behind their respective retaining flanges 88f on the pressure jacket 88.

In FIG. 10, in which the injector drive member 48' is in a forward position, the mounting of the syringe 22' into the pressure jacket 88 is the same as shown in FIG. 9, except that the plunger 38' also is in its forward position in the syringe. In other respects, the mounting of the syringe 22' on the pressure jacket 88 is essentially the same as previously described for FIG. 9. However, having the syringe plunger 38' and the drive member 48' in their forward positions, as shown in FIG. 10, has several advantages over the rearward position arrangement of FIG. 9, from a time standpoint. For example, since the syringe plunger 38' and the drive member 48' are already in their forward positions, it is not necessary to move them forward in preparation for a syringe-filling operation; rather, the plunger and the drive member can immediately be retracted for this purpose. Similarly, after an injection operation has been completed, additional time is saved by not having to retract the plunger 38' and the drive member 48' in preparation for a next injection operation. Further, this embodiment prevents the drive member 48' from touching or contaminating the inner wall of syringe 22'.

In summary, a new and improved system by which an injection syringe, such as the syringe 22 in the embodiment of FIGS. 1–8, readily can be mounted upon and/or removed from the front wall 24 of the injector housing 26, has been disclosed. For this purpose, the first readily releasable mechanism 28, by which the syringe 22 is attached to or removed from the injector housing front wall 26, and the second readily releasable mechanism 42, by which the plunger 38 of the syringe is drivingly connected to or released from the drive member 48 of the injector 27 cooperate to produce their respective connections and disconnections simultaneously. Another advantage is that the plunger 38 is capable of being placed in a driven or undriven state at any point along its path, whereby the syringe 22 may be disengaged from the injector 27 without having to retract the drive member, or having to first disconnect the syringe from an animal being injected before retracting the drive member.

Other desirable features of the invention include the construction of the first readily releasable mechanism 28, in which the syringe 22 is mounted upon the front wall 24 of the injector housing 26 with an interference friction fit, which is advantageous from the standpoint of minimizing syringe wobble and reverse rotation (disengagement) during an injection operation, and eliminating the need for excessively tight manufacturing tolerances. Proper mounting of the syringe 22 and prevention of disengagement also is facilitated by the audible-and-tactile detecting mechanism 64. The encoding device 70 on the syringe 22, in cooperation with the sensor 72 on the injector 27, also is advantageous from the standpoint of providing "custom programming" of the injector as they syringe is mounted thereon. Elimination of a pressure jacket also is desirable from the standpoint of better visibility of the contents of the syringe 22, better heat transfer to the syringe contents and decreased cleaning and maintenance otherwise needed due to, e.g., scratching or contamination with contrast media of the pressure jacket.

In order to eliminate the need for a pressure jacket, the syringe 22 also may be made of a relatively strong clear plastic, or may be provided with the annular reinforcing ribs 74, which also are spaced to functions as volumetric gradations, as disclosed in FIG. 5. Further, the detection of the presence of liquid in the syringe 22 is facilitated by the indicating mechanism 76 in FIG. 6, in the form of the dots 78 molded into the syringe tubular body 32, with the dots appearing visually as either oval-shaped or circular, depending upon whether the tubular body contains air or liquid, respectively. In addition to functioning as a part of the first readily releasable mechanism 28 for the syringe 22, the syringe resilient annular flange 60 also cooperates with the annular ring 58 to create a seal to prevent contrast media spilled from the injection end of the syringe, from flowing into the injector housing 26, as shown in FIG. 7. The embodiment of the invention shown in FIGS. 9 and 10 also provides a system by which various other advantages, including time savings in syringe-filling and syringe-changing operations, can be achieved utilizing a pressure jacket, such as the pressure jacket 88 mounted in the connector assembly 23' on the injector housing front wall. 24'.

While the injector apparatus of the present invention is especially designed for injection, it may be applicable to other systems, angiographic and otherwise. It is therefore understood that the foregoing description and accompanying drawings set forth the preferred embodiments of the invention at the present time. Various modifications, additions and alternative designs will, of course, become apparent to those skilled in the art in light of the foregoing teachings without departing from the spirit and scope of the disclosed invention. Thus, it should be appreciated that the invention is not limited to the disclosed embodiments but may be practiced within the full scope of the appended claims.

What is claimed is:

1. An injector system comprising:
   an injector comprising:
      a housing containing a motor operable to drive a piston,
      a sensor, and
      a control unit in communication with the sensor and the motor; and
   a syringe comprising:
      a body comprising a front end and a rear end;
      a plunger disposed within the body and operable to be driven by the piston of the injector; and
      an encoding device on the plunger and operable to provide syringe information to the sensor,
   whereby the sensor is operable to read the syringe information provided by the encoding device and to forward the syringe information to the control unit of the injector, the control unit operable to receive the syringe information from the sensor and to control the motor of the injector based on the syringe information.

2. The injector system of claim 1 wherein the encoding device comprises a bar code.

3. The injector system of claim 1 wherein the encoding device comprises an optically readable device.

4. The injector system of claim 1 wherein the syringe information comprises liquid media information.

5. The injector system of claim 1 wherein the syringe information comprises liquid media injection information.

6. The injector system of claim 1, further comprising at least one mounting flange associated with the body.

7. The injector system of claim 6 wherein the at least one mounting flange is associated with the rear end of the body.

8. The injector system of claim 6, further comprising a flange member associated with the body between the at least one mounting flange and the front end of the body.

9. The injector system of claim 6 wherein the injector housing defines at least one retaining flange operable to be engaged by the at least one mounting flange to retain the syringe on the injector.

10. The injector system of claim 1 wherein the syringe information comprises the dimensions of the syringe.

11. The injector system of claim 1 wherein the syringe information comprises the contents of the syringe.

12. The injector system of claim 1 wherein the syringe information comprises flow rates.

* * * * *